United States Patent
Jornitz et al.

(10) Patent No.: US 9,072,996 B2
(45) Date of Patent: Jul. 7, 2015

(54) METHOD AND APPARATUS FOR CARRYING OUT INTEGRITY TESTS OF A NON-WETTED FILTER ELEMENT

(75) Inventors: Maik Jornitz, Manorville, NY (US); Jens Meyer, Moringen (DE)

(73) Assignee: Sartorius Stedim Biotech GmbH (DE)

( * ) Notice: Subject to any disclaimer, the term of this patent is extended or adjusted under 35 U.S.C. 154(b) by 641 days.

(21) Appl. No.: 13/128,702

(22) PCT Filed: Oct. 21, 2009

(86) PCT No.: PCT/EP2009/007529
§ 371 (c)(1),
(2), (4) Date: May 13, 2011

(87) PCT Pub. No.: WO2010/054740
PCT Pub. Date: May 20, 2010

(65) Prior Publication Data
US 2011/0214485 A1    Sep. 8, 2011

(30) Foreign Application Priority Data
Nov. 14, 2008  (DE) .......................... 10 2008 057 458

(51) Int. Cl.
*G01M 3/24* (2006.01)
*B01D 46/00* (2006.01)
(Continued)

(52) U.S. Cl.
CPC ........ *B01D 46/0086* (2013.01); *B01D 46/2407* (2013.01); *B01D 46/44* (2013.01); *B01D 2273/24* (2013.01); *G01N 2015/084* (2013.01)

(58) Field of Classification Search
CPC .......... B01D 2273/18; B01D 2273/24; G01N 2015/084
USPC ................................ 73/40.5 A, 587, 592, 38
See application file for complete search history.

(56) References Cited

U.S. PATENT DOCUMENTS 4,701,861 A * 10/1987 Kauke ........................... 700/266
4,744,240 A   5/1988 Reichelt
(Continued)

FOREIGN PATENT DOCUMENTS

DE    694 09 736    10/1998
EP    0 248 218     12/1987
(Continued)

OTHER PUBLICATIONS

International Preliminary Report on Patentability.

*Primary Examiner* — Peter Macchiarolo
*Assistant Examiner* — Natalie Huls
(74) *Attorney, Agent, or Firm* — Gerald E. Hespos; Michael J. Porco; Matthew T. Hespos

(57) ABSTRACT

A method and an apparatus are provided for carrying out integrity tests of at least one filter element, arranged within a filter housing, with porous filter materials. Sensors are provided for measuring the sound generated by a test fluid when it flows through the filter element. The method includes applying a test fluid to a first side of the filter materials of the filter element while maintaining a constant fluid pressure, measuring the body-borne sound and/or the vibrations caused by test fluid flowing through the filter materials by sensors, and comparing the body-borne sound and/or the vibrations with the body-borne sound and/or the vibrations of an integral, identical filter element, measured under identical conditions.

8 Claims, 2 Drawing Sheets

(51) Int. Cl.
    *B01D 46/24*    (2006.01)
    *B01D 46/44*    (2006.01)
    *G01N 15/08*    (2006.01)

(56) References Cited

U.S. PATENT DOCUMENTS

| | | | |
|---|---|---|---|
| 5,205,156 A * | 4/1993 | Asano et al. | 73/38 |
| 5,417,101 A * | 5/1995 | Weich | 73/38 |
| 5,576,480 A * | 11/1996 | Hopkins et al. | 73/38 |
| 5,581,017 A * | 12/1996 | Bejtlich, III | 73/38 |
| 6,370,943 B1 * | 4/2002 | Glucina et al. | 73/38 |
| 6,568,282 B1 | 5/2003 | Ganzi | |
| 6,666,070 B1 * | 12/2003 | Hagg et al. | 73/38 |
| 7,048,775 B2 * | 5/2006 | Jornitz et al. | 95/1 |
| 7,281,409 B2 * | 10/2007 | Baumfalk et al. | 73/38 |
| 7,360,400 B2 * | 4/2008 | Baumfalk et al. | 73/38 |
| 2004/0237654 A1 * | 12/2004 | Savall et al. | 73/592 |
| 2005/0012935 A1 * | 1/2005 | Kersey | 356/519 |
| 2007/0101802 A1 * | 5/2007 | Biggs | 73/38 |

FOREIGN PATENT DOCUMENTS

| | | |
|---|---|---|
| EP | 0 640 822 | 8/1994 |
| JP | 2006-218372 | 8/2006 |
| WO | 94/11721 | 5/1994 |
| WO | 99/16538 | 4/1999 |

* cited by examiner

METHOD AND APPARATUS FOR CARRYING OUT INTEGRITY TESTS OF A NON-WETTED FILTER ELEMENT

BACKGROUND OF THE INVENTION

1. Field of the Invention

The invention relates to a method for carrying out integrity tests of at least one filter element, arranged within a filter housing, with porous filter materials, in which means are provided for measuring the sound generated by a test fluid when it flows through the filter element.

2. Description of the Related Art

The invention furthermore relates to an apparatus for carrying out integrity tests of at least one filter element, arranged within a filter housing, with porous filter materials, in which means are provided for measuring the sound generated by a test fluid when it flows through the filter element.

WO 94/11721 A1 has disclosed an apparatus and a method for carrying out integrity tests of filter elements, arranged within a filter housing, with porous filter material. There, a filter element wetted by a wetting solution subdivides a housing interior into an inlet side, or an unfiltrate space, and an outlet side, or filtrate space. Both sides can be filled with a test fluid, a pressure difference being generated between the inlet side and outlet side such that the test fluid flows through the filter element, with sound generated in the process being recorded by a sensor or a microphone, which is arranged in the vicinity of the wetted filter element or in the lumen of an inlet pipe or an outlet pipe, and being routed to a signal-processing unit as an electrical signal. The signal-processing unit analyzes the signal and determines whether or not the filter element is integral.

A disadvantage of this is that a test is carried out in this case that requires a wetted filter. The utilized pressure difference, or the pressure provided for flowing through the filter element, must in this case be less than the pressure at which the wetting agent is driven out of the largest pore of a homogenously porous structure of the filter material.

Furthermore, EP 0 248 218 B1 likewise discloses a method and an apparatus for carrying out integrity tests, in which a filter element, for example a hollow-fiber membrane, is arranged in a housing interior. In this case, a so-called bubble point test is also carried out. To this end, the filter material must in this case also be wetted by a wetting liquid. As the gas-space pressure increases with time, the sound intensity in a housing interior filled with a liquid is measured by a microphone, with the gas-space pressure being determined at which a jump-like increase in the sound intensity can be determined.

Furthermore, WO 99/16538 A1 discloses an apparatus and a method for localizing defective filter elements within a plurality of filter elements arranged within a housing. All filter elements arranged in a housing are also wetted by a liquid in this case and are subjected to a gas pressure, with the presence of defective filter elements being identified acoustically during a diffusion test by means of microphones.

Furthermore, JP 2006-218372 A (abstract) has disclosed a method and an apparatus for carrying out integrity tests of membrane filters arranged within a filter housing. The membrane filters subdivide a membrane module or a filter housing into an unfiltrate space and a filtrate space. A flow of gas between the two chambers can be determined by means for measuring sound generated in the membrane module.

This also has the disadvantage that the filter elements appear to have to be wetted.

U.S. Pat. No. 6,666,070 B1 has disclosed a method and a device for identifying integrity defects in the form of leaks in a honeycomb structure of a filter for capturing and burning diesel exhaust-gas particles. The honeycomb structure of the filter comprises a plurality of parallel cell channels, which traverse the honeycomb structure from an inlet end to an outlet end. In order to carry out the integrity test, compressed air is introduced through the inlet end of the honeycomb structure. An acoustic sensor is arranged at the outlet end of the honeycomb structure, and it identifies an airflow at the outlet end.

A disadvantage here is that the filter has a porosity that does not permit the compressed air to pass through the internal walls as long as there are no leaks. The air blower utilized in the process has a pressure that should lie between 1 and 15 psi. The fluid pressure acting on the filter materials changes depending on the leaks present, even in the case of an air blower operating at a fixedly set value. A further disadvantage is that the filter has to be inserted into a special test housing for the test.

DE 694 09 736 T2 has disclosed a method for carrying out integrity tests of a filter element, arranged within a filter housing, with a porous filter material; in the process, a gas mixture is applied onto a surface of the filter or the membrane structure under pressure in order to prompt the gas mixture to migrate through the pores in the membrane structure and emerge from a second surface of the same.

A disadvantage here is that in order to generate an acoustic emission, components of the gas mixture or of the test fluid, after emerging from the second surface, have to be excited by a light beam at a wavelength that is strongly absorbed by the component of the gas mixture. A further disadvantage is that this test also requires a wetted filter.

U.S. Pat. No. 6,568,282 B1 has disclosed a method for carrying out integrity tests on a filter, which is embodied as a porous membrane spanned in a housing. In the method, a fluid, which at least in part cannot be mixed with the wetting fluid used for the membrane, is supplied to a first side of the wetted membrane at a pressure that is higher than a pressure on a second side of the membrane. In the process, a predetermined pressure difference is set in the membrane or filter housing, and the transmission speed of the test fluid is subsequently measured from the first side of the membrane to the second side of the membrane. The measured transmission speed is subsequently compared to a second, predetermined transmission speed in order to determine the integrity.

It is also disadvantageous here that it requires a wetting of the filter material. Measuring sound has not been disclosed in this document, and there is no point in doing so on account of the utilized measurement principle.

Thus, it is an object of the present invention to specify a method and an apparatus that do not have the aforementioned disadvantages and wherein, more particularly, it is possible to carry out the method with unwetted filter elements.

SUMMARY OF THE INVENTION

The invention relates to a method for carrying out integrity tests of at least one filter element arranged within a filter housing with porous filter materials in which means are provided for measuring the sound generated by a test fluid when it flows through the filter element. The method is characterized by a) applying a test fluid to a first side of the filter materials of the filter element while maintaining a constant fluid pressure, b) measuring the body-borne sound and/or the vibrations caused by test fluid flowing through the filter materials by means of sensors, and c) comparing the body-borne sound and/or the vibrations measured in step b) with the body-borne sound and/or the vibrations of an integral, identical filter element, measured under identical conditions.

In contrast to the known test methods such as the bubble point test and diffusion test, the method according to the invention does not require the filter elements to be wetted prior to the test. The noise or the sound of the fluid flow according to the invention varies in terms of its spectral composition or frequencies and/or in terms of its amplitude, should changes occur in the filter system that can be used to determine the integrity of the entire filter system or of an individual filter element. In the process, the sound is measured indirectly as a body-borne sound or vibration, respectively caused by the test fluid flowing through the filter materials. The basis of the sound strength and the spectrum thereof can be determined by comparing the measured body-borne sound and/or the frequencies or vibrations to sound and/or vibrations of an integral, identical filter element measured under identical conditions. As a result, the integrity of a filter element can be tested in a relatively simple and reliable fashion.

As per a preferred embodiment of the invention, a test liquid can be used as test fluid. However, it is particularly advantageous to use a test gas as test fluid. For this, unlike in the known tests, it is unnecessary to wet the filter elements in advance.

The body-borne sound can be measured with the aid of sensors, which are arranged on a filter-housing wall and/or on inflow or outflow lines.

As per a further preferred embodiment of the invention, the body-borne sound is measured contactlessly by laser vibration measurement.

According to a further preferred embodiment of the invention, vibration patterns are measured, which are generated at the filter elements and/or at the filter housing and/or at the inflows and/or outflows. Here, the vibration patterns can be measured by vibration sensors, which are arranged directly on the filter elements, the filter housing or on the inflow or outflow.

However, as per a further preferred embodiment of the invention, the vibration patterns can also be measured contactlessly by optical vibration sensors. In particular, the vibration patterns can be determined contactlessly by a laser vibration measurement.

The invention also relates to an apparatus for carrying out integrity tests of at least one filter element arranged within a filter housing with porous filter materials in which means are provided for measuring the sound generated by a test fluid when it flows through the filter element. To measure the sound as body-borne sound, sensors are provided on the filter-housing wall and/or on the inflow or outflow lines, and/or to measure vibrations generated by the sound contactless sensors are provided.

As a result of using contactless sensors as means for measuring the sound, sensors can also be dispensed with in the housing, the filter element or the inflows and outflows. The contactless sensors are reusable, while the filter housing with filter element, or at least the filter element, can be replaced in a cost-effective fashion, for example as a disposable filter element.

As per a preferred embodiment of the invention, the sensors are optical vibration sensors in conjunction with a laser vibration measurement.

Further features of the invention emerge from the following detailed description and the attached drawings, in which preferred embodiments of the invention are illustrated in an exemplary fashion.

DETAILED DESCRIPTION OF THE PREFERRED EMBODIMENTS

Figure 1:
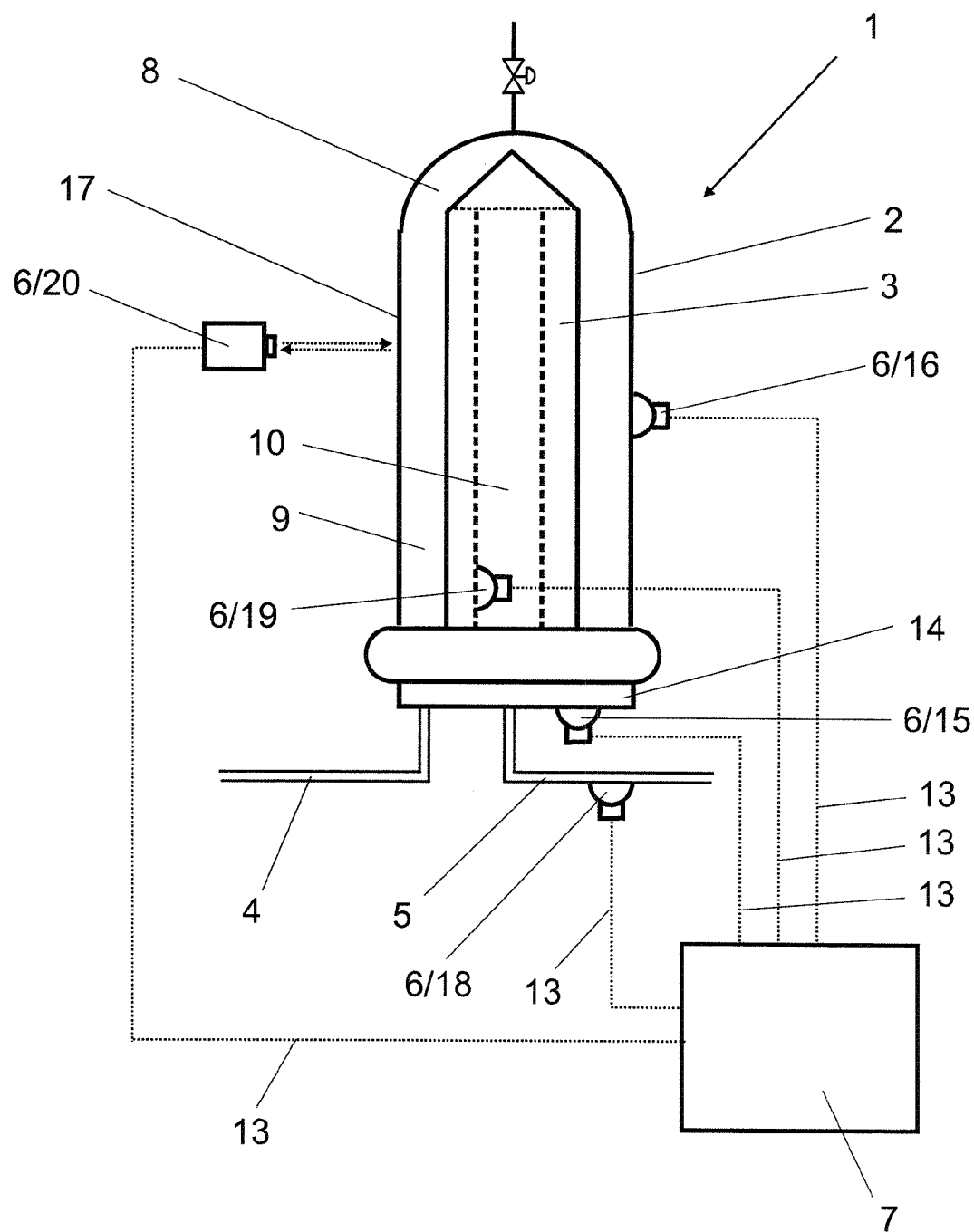
FIG. 1 is a schematic lateral view of an apparatus for carrying out integrity tests with an individual filter element and FIG. 2 is a schematic lateral view of an apparatus for carrying out integrity tests with a housing with three filter elements.

An apparatus 1 for carrying out integrity tests consists essentially of a housing 2, a filter element 3, an inflow 4, an outflow 5, sensors 6 and a signal-processing unit 7.

In accordance with the exemplary embodiment in FIG. 1, the filter element 3 is arranged in a housing interior 8 of the housing 2. The filter element 3 with porous filter material subdivides the housing interior 8 into an unfiltrate space 9 and a filtrate space 10 arranged centrally in the filter element 3. The unfiltrate space 9 is connected to the inflow 4 and the filtrate space 10 is connected to the outflow 5. The sensors 6 are connected to the signal-processing unit 7 via signal lines 13. The signal lines 13 can also be embodied as wireless connections.

Even though a plurality of sensors 6 have been illustrated in FIG. 1, a single sensor 6 suffices to carry out an integrity test with a single filter element 3.

A sensor 15 arranged on the outside of the base plate has proven its worth for measuring body-borne sound or vibrations. It is also possible to arrange a sensor 16 externally on the housing wall 17 of the housing 2 for the purposes of measuring the body-borne sound or vibrations.

A further sensor 18, which may be arranged externally on the outflow 12 or within the outflow 5, is shown in an exemplary fashion. It is also possible to arrange a sensor 19 in the filter element 3 or in the filtrate space 10.

A contactless sensor 20, which optically scans the housing wall 17 of the housing 2 and transmits the measured vibrations of the housing wall 17 to the signal-processing unit 7 via the signal line 13, is furthermore illustrated in FIG. 1 in an exemplary fashion.

Figure 2:
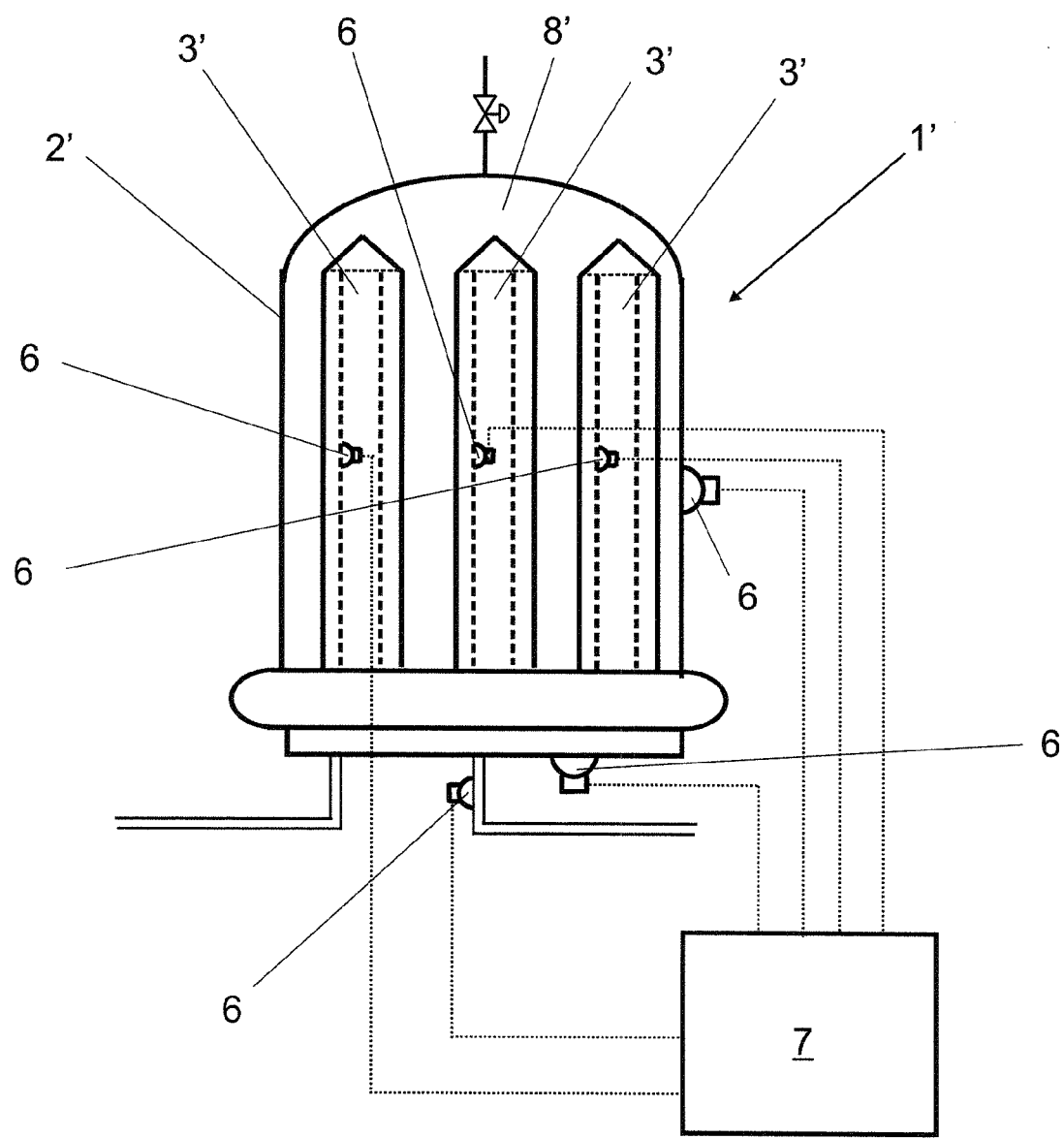

The exemplary embodiment in FIG. 2 shows an apparatus 1' with a housing 2', with three filter elements 3' being arranged in the housing interior 8' thereof. If only one sensor 6 used, it is at least possible to determine whether the group of three filter elements 3' are integral when an integrity test is carried out. A sensor 6 is associated with each filter element 3' insofar as the integrity of an individual filter element 3' should also be determined.

In order to carry out an integrity test, a test fluid is supplied to the unfiltrate space 9 via the inflow 4, while maintaining a constant fluid pressure, such that the fluid pressure acts on a first side, facing the unfiltrate space 9, of the filter materials of the filter element 3, 3'. In the process, the test fluid flows through the filter element 3, 3', or the filter materials thereof, and causes sound or vibrations. In the process, the sound caused and/or the vibration is/are measured by the sensors 6 and, in a subsequent step including the measured sound and/or the vibration, is/are compared to the sound and/or the vibration of an integral, identical filter element, measured under identical conditions. That is to say the sound or the vibration is detected by the sensors 6 and transmitted via the signal line 13 to the signal-processing unit 7, in which sound or vibration values measured under identical conditions are stored, and so a comparison can take place in the signal-processing unit 7.

The invention claimed is:

1. A method for carrying out integrity tests of at least one filter element (3, 3') arranged within a filter housing (2, 2') between an unfiltrate space (9) and a filtrate space (10), with porous filter materials, in which means are provided for measuring sound generated by a test fluid when the test fluid flows through the filter element (3, 3'), the method comprising:
   a) applying a test fluid that is a gas to a first side of the filter materials of the filter element (3, 3') while the filter materials are in a not wetted state and while maintaining a constant fluid pressure sufficient to cause the test fluid to flow through the filter materials from the first side to a second side opposite the first side while maintaining the filter materials in the not wetted state,
   b) measuring at least one of body-borne sound and vibrations caused by the test fluid flowing through the filter materials by means of sensors (6, 15, 16, 18, 19, 20), and
   c) comparing at least one of the body-borne sound and the vibrations measured in step b) with at least one of the body-borne sound and the vibrations of an integral, identical filter element (3, 3'), measured under identical conditions.

2. The method of claim 1, characterized in that the body-borne sound is measured with the aid of sensors (6, 15, 16, 18, 19, 20) arranged on a filter-housing wall (17) of the filter housing (2, 2') or on inflow (4) or outflow lines (5).

3. The method of claim 1, characterized in that the body-borne sound is measured contactlessly by laser vibration measurement.

4. The method of claim 1, characterized in that vibration patterns are measured that are generated at the filter elements (3, 3') or at the filter housing (2, 2') or at the inflows (4) and/or outflows (5).

5. The method of claim 4, characterized in that the vibration patterns are measured by vibration sensors (6, 18, 19, 20) that are arranged directly on the filter elements (3, 3'), the filter housing (2, 2') or the inflow (4) or outflow (5).

6. The method of claim 4, characterized in that the vibration patterns are measured contactlessly by optical vibration sensors (20).

7. The method of claim 6, characterized in that the vibration patterns are measured by a laser vibration measurement.

8. The method of claim 1, wherein the step of measuring at least one of body-borne sound and vibrations caused by the test fluid flowing through the filter element (3, 3') is carried out by measuring at least one of body-borne sound and vibrations at a base plate (14) through which an inlet (4) to the filter housing (2, 2') and an outlet (5) from the filter housing (2, 2') extend.

* * * * *